United States Patent [19]

Andersson

[11] Patent Number: 4,557,265
[45] Date of Patent: Dec. 10, 1985

[54] SUTURING INSTRUMENT

[75] Inventor: Leif Andersson, Norrahammar, Sweden

[73] Assignee: Innova AB, Norrahammar, Sweden

[21] Appl. No.: 574,215

[22] Filed: Jan. 26, 1984

[30] Foreign Application Priority Data

Feb. 8, 1983 [SE] Sweden ................................ 8300654

[51] Int. Cl.⁴ ...................... A61B 17/04; A61B 17/06; D05C 15/04; D05C 15/16
[52] U.S. Cl. .................................. 128/340; 128/339; 112/80; 112/222
[58] Field of Search ................... 128/340, 339; 112/80, 112/222, 227

[56] References Cited

U.S. PATENT DOCUMENTS

| | | | |
|---|---|---|---|
| 919,138 | 4/1909 | Drake et al. | 128/340 |
| 2,439,393 | 4/1948 | Erickson | 128/340 |
| 3,344,790 | 10/1967 | Dorner | 112/80 |
| 4,109,658 | 8/1978 | Hughes | 128/340 |
| 4,345,601 | 8/1982 | Fukuda | 128/334 R |

OTHER PUBLICATIONS

Singer Surgical Stitching Instrument, Singer Sewing Machine Co., Apr. 29, 1944, Div. 55.

Primary Examiner—D. E. Gantz
Assistant Examiner—Helane Myers
Attorney, Agent, or Firm—Sughrue, Mion, Zinn, Macpeak and Seas

[57] ABSTRACT

The invention relates to suturing instrument for joining two edges of biological tissue together. The instrument includes a housing (1) in which there is movably arranged an arcuate suture needle (16) having a point (17) arranged to penetrate the tissue, and the suture thread (18) connected to the suture needle. Drive means (3,8,11,12,13) are provided for causing the needle (16) to move in a manner such as to pass the thread thereon through one of the tissue edges and up through the other of the tissue edges, to join the two edges together with a firm suture. The novel feature of the instrument resides in the fact that the end of the suture needle remote from the point (17) thereof is connected to the suture thread and is arranged to be driven in the direction of the point (17) in a closed path by the drive means.

5 Claims, 5 Drawing Figures

U.S. Patent Dec. 10, 1985 4,557,265
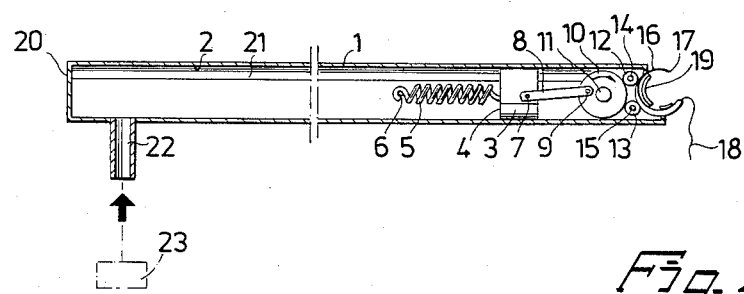
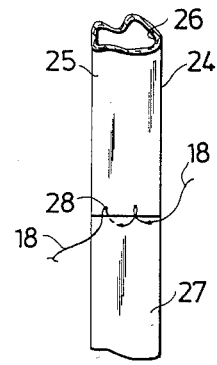
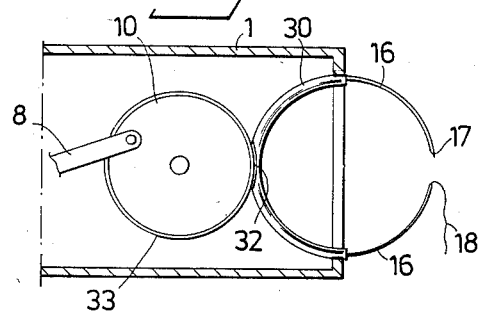
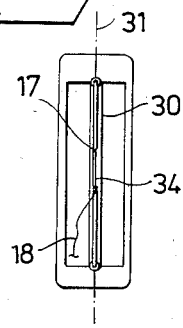
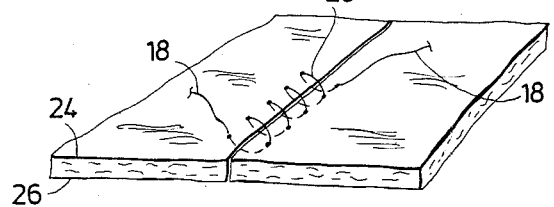

SUTURING INSTRUMENT

The invention relates to a suturing instrument for joining together two edges of biological tissue, said instrument comprising an instrument housing in which there is movably arranged an arcuate suturing needle having a sharp point for penetrating the tissue, and a suture thread connected to the suturing needle, and further comprising drive means for moving the needle in a manner to pass the thread down through one edge of said tissue and up through the other of said edges, so as to join the edges together with a firm suture.

Suturing instruments of this kind are known, for example, from U.S. Pat. No. 2 959 172, but have not found wide use. One reason for this is that such instruments are relatively difficult to use, and are not suitable for suturing work of a delicate, complicated nature, for example work involving the suturing of blood vessels. In this latter case, it has hitherto been necessary to manoeuver a needle with the aid of pincettes, thereby extending the time required to carry out the operation.

Consequently, a prime object of the invention is to provide a suturing machine which can be used readily, even in cases of microsurgery, and which sews a very fine suture, both with respect to a single surgical stitch and a row of such stitches; and which can be used effectively to stitch vessels and nerves, but which, nevertheless, can still be used in any conventional circumstance of a less delicate nature, such as suturing stomach incisions, for example.

This object is realized to the full by the invention set forth in the following claims and hereinafter discribed with reference to the accompanying drawing, in which FIG. 1 is a simplified view of a suturing instrument according to the invention;

FIG. 2 illustrates the joining of a blood vessel;

FIG. 3 illustrates the mode of the instrument in sewing two edges of tissue together;

FIG. 4 illustrates part of a modified instrument according to the invention, and FIG. 5 illustrates the instrument shown in FIG. 4, seen towards the needle-carrying end thereof.

The instrument illustrated in FIG. 1 includes a tubular instrument housing 1 of circular, elliptical or rectangular cross-section. The housing 1 is preferably made of metal and, in the illustrated embodiment, has a cylindrical interior in which there is arranged a movable plunger 3, which seals against the inside wall 2 of the housing 1. The rear end 4 of the plunger 3, said end wall facing to the left in the figure, is connected to one end of a return spring 5, the upper end of which is connected to a pin 6 firmly anchored in the housing 1. The plunger 3 has a plunger rod 8 which can be swung about a fixed shaft 7 on said plunger. The free end of the plunger rod is pivotally mounted a peg 9, which is mounted eccentrically on a flywheel 10. The flywheel 10 is mounted for rotation on a shaft 11, which is fixedly mounted on the housing 1. Coacting with the periphery of the cylindrical flywheel 10 are two, freely-rotating friction rollers 12 and 13 journalled on shafts 14 and 15, which extend parallel with the shaft 11 and which, similar to said shaft, are mounted on the housing 1. A circular-arcuate suture needle 16 having a sharp point 17 on one end thereof and a suture thread 18 connected to the other end thereof is arranged to co-act with guide means 19 diagrammatically illustrated in FIG. 1, and can be driven around a circular part with the pointed end 17 of the needle in the driving direction. The rear end 20 of the housing 1 is closed, and between said end and the rear end surface 4 of the plunger is formed a cylindrical space 21. The cylindrical space 21 is connected to a diagrammatically illustrated drive source 23, via a line 22. The drive source 23 is arranged to deliver a pressure surge to the cylinder space 21 at, for example, pre-determined or randomly selected time intervals, whereupon the plunger 3 is urged forwards. The drive source may, for example, be coupled to a foot pedal, arranged to cause the delivery of a pressure surge each time it is depressed. When the plunger moves towards the needle 16, under the action of the increased pressure in the cylinder space 21, the flywheel 10 will rotate and its rotary motion transmitted to the two friction rollers 12 and 13 abutting the suture needle 16. As a result hereof, the circular-arcuate suture needle 16 is rotated about its centre axis, with the point 17 of the needle in the rotating direction. As soon as the plunger rod 8 reaches its top-dead-centre position, the pressure surge is interrupted and the pressure in the cylinder space 21 will fall, whereupon the return spring 5, which is now tensioned, will function to withdraw the plunger 10 back to its inner position. By suitable adjustment of the duration of the pressure surge, the flywheel 10 can be given a continuous rotary movement, and the point 17 of the needle will carry out one revolution for each pressure surge and subsequent release of the return spring 5, thereby to provide a working cycle in which the needle point is passed down through the upper surface 24 of the one tissue part 25 and from the lower surface 26 of the adjacent tissue part 27. Thus, the suture thread forms a loop through the two tissue parts and, as illustrated in FIGS. 2 and 3, forms a continuous suture 28 by repeating the aforedescribed working cycle.

FIGS. 4 and 5 illustrate a modification of the instrument illustrated in FIG. 1. In the FIGS. 4 and 5 embodiment the needle 16 is also of circular arcuate shape and is guided in a thin tube 30 having the same curvature as the needle 16. To enable the thread 18 to run freely, the inner periphery part of the tube 30 is slotted, as shown in FIG. 5. The tube 30 embraces the needle at such a large angle, for example an angle of 180°, that the needle is constantly held in its plane 31. The rear part of the tube 30 is cut away, so as to form a free opening 32 through which the needle 16 can be reached. The flywheel 10 is peripherially in contact with that part of the needle 16 lying in the opening 32, the periphery of the flywheel 10 being covered with a layer 33 of rubber or like material so as to provide good frictional contact. Since, in this case, only one drive roller is used, namely the flywheel 10, the extent to which it abuts the rear side of the needle 16 must exceed the gap between the point 17 of the needle and the end of said needle connected to the thread 18, so as to obtain a constant drive. If the needle gap is greater than the distance over which the flywheel 10 abuts the needle 16, there are used two or more drive rollers according to the FIG. 1 embodiment, of which drive rollers at least one is constantly in driving connection with the needle.

The aforedescribed pneumatic needle-drive can be replaced with any other suitable drive arrangement. Thus, for example, there may be provided an electric motor on whose drive shaft is arranged a drive disc which is in friction contact with the needle and which drives said needle around its path in response to current supplied to the motor. The needle 16, which is made of a resilient, preferably stainless wire of circular cross-section, need not be of circular-arcuate shape along the whole of its length. The only essential feature of the needle is that the point 17 thereof moves in a circular path externally of the instrument housing.

The forward part of the housing 1, which holds the needle and its guide means, may suitably be made detachable, so as to enable needles of varying sizes to be used with the instruments.

I claim:

1. A suturing instrument for joining together two edges of biological tissue, which comprises an instruments housing (1), in which there is movably arranged an arcuate suture needle (16) having a point (17) arranged to penetrate the tissue and a suture thread (18) connected to said needle (16); and further comprising drive means (3,8,11,12,13) for moving the suture needle (16) in a manner to pass the suture thread (18) down through one of said tissue edges and up through the other of said tissue edges, thereby to join the two tissue edges together with a firm suture, characterized in that the end of the suture needle remote from said point (17) is connected to the suture thread (18) and arranged to be driven by the drive means in a closed path in the direction of said point (17).

2. An instrument according to claim 1, characterized in that the suture needle (16) is of circular-arcuate configuration, and is mounted in guide means (19;30) arranged to guide the point of the needle externally of the instrument in a circular-arcuate path during movement of said suture needle.

3. An instrument according to claim 1 or claim 2, characterized in that the drive means is arranged to drive the suture needle stepwise, so that the point (17) of the needle (16) is moved a complete revolution in said closed path during each step.

4. An instrument according to claim 1 or claim 2, characterized in that the drive means is arranged to cause the suture needle to move continuously in its closed path.

5. An instrument according to anyone of claims 1–4, characterized in that the needle is caused to move by frictional contact with at least one driven friction roller (10;12,13).

* * * * *